United States Patent
Fray et al.

(10) Patent No.: US 9,028,671 B2
(45) Date of Patent: May 12, 2015

(54) HYDROGEN SENSING APPARATUS AND METHOD

(75) Inventors: Derek John Fray, Cambridge (GB); Carsten Schwandt, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 0 days.

(21) Appl. No.: 13/187,207

(22) Filed: Jul. 20, 2011

(65) Prior Publication Data

US 2012/0037516 A1 Feb. 16, 2012

Related U.S. Application Data

(63) Continuation of application No. 10/527,347, filed on Mar. 10, 2005, now abandoned.

(30) Foreign Application Priority Data

Sep. 14, 2002 (GB) .................................. 0221393.2

(51) Int. Cl.
*G01N 27/26* (2006.01)
*G01N 33/00* (2006.01)
*G01N 27/407* (2006.01)

(52) U.S. Cl.
CPC .......... *G01N 33/005* (2013.01); *G01N 27/4074* (2013.01)

(58) Field of Classification Search
USPC .......................................... 205/789; 204/427
See application file for complete search history.

(56) References Cited

U.S. PATENT DOCUMENTS

| 4,127,443 | A | | 11/1978 | Wetch et al. |
| 4,174,258 | A | | 11/1979 | Bode |
| 4,664,757 | A | | 5/1987 | Zupancic et al. |
| 4,882,032 | A | | 11/1989 | Tiwari |
| 5,344,548 | A | | 9/1994 | Alberti et al. |
| 5,445,725 | A | | 8/1995 | Koide et al. |
| 5,453,172 | A | | 9/1995 | Alberti et al. |
| 5,733,828 | A | * | 3/1998 | Usui et al. ........................ 501/17 |

FOREIGN PATENT DOCUMENTS

| EP | 0 330 249 A2 | 8/1989 |
| GB | 1 234 922 A | 6/1971 |

OTHER PUBLICATIONS

Katahira, K. et al. "A Solid Electrolyte Hydrogen Sensor with an Electrochemically-Supplied Hydrogen Standard" *Sensors and Actuators B*, Mar. 10, 2001, pp. 130-134, vol. 73, No. 2-3.

Schwandt, C. et al. "A Novel Electrochemical Hydrogen Analyser for use in Molten Aluminum and its Alloys" *6th International American Foundry Society Conference*, Orlando, 2001, pp. 149-157.

(Continued)

*Primary Examiner* — Keith Hendricks
*Assistant Examiner* — Kourtney S Carlson
(74) *Attorney, Agent, or Firm* — Saliwanchik, Lloyd & Eisenschenk (57) ABSTRACT

An apparatus and methods are provided for the accurate determination of hydrogen content in fluid media at elevated temperatures. The apparatus consists of a proton conducting solid electrolyte in contact with an internal metal/hydrogen reference standard, in which the electrolyte and the reference material are in a chemically stable contact. The electrical signal generated is a function of the hydrogen concentration on the measuring side.

21 Claims, 4 Drawing Sheets

(56) References Cited

OTHER PUBLICATIONS

Yajima, T. et al. "$CaZrO_3$-Type Hydrogen and Steam Sensors: Trial Fabrication and Their Characteristics" *Sensors and Actuators B*, Aug. 1, 1991, pp. 145-147, vol. B05, No. 1/4.

"Electronic and Specialty Glass: Low Temperature Sealing." Ferro Corporation. 2008. Apr. 11, 2008. http://www.ferro.com/our+products/electronic/products+and+markets/electronic+and+specialty+glass/low-temperature+sealing.htm.

* cited by examiner

HYDROGEN SENSING APPARATUS AND METHOD

CROSS-REFERENCE TO RELATED APPLICATIONS

The present application is a continuation of U.S. application Ser. No. 10/527,347, filed Mar. 10, 2005, which is the U.S. national stage application of International Patent Application No. PCT/GB2003/003967, filed Sep. 12, 2003, each of which is hereby incorporated by reference herein in its entirety, including any figures, tables, nucleic acid sequences, amino acid sequences, or drawings.

FIELD OF INVENTION

The present invention relates to apparatus and a method for measuring the concentration of hydrogen in fluid media at elevated temperatures using a high temperature proton-conducting solid electrolyte in conjunction with an internal hydrogen standard.

BACKGROUND OF THE INVENTION

The monitoring and control of hydrogen concentration in gaseous and liquid media is an important technological issue. Fields of application include, for instance, the analysis of gas composition on the fuel side of hydrogen-based fuel cells and the determination of dissolved hydrogen content in molten metals like aluminium. It is therefore desirable to develop simple, easily applicable, reliable and inexpensive sensors having high sensitivity and selectivity.

One concept of constructing hydrogen sensors for operation at elevated temperatures is to utilise a proton conducting solid electrolyte that compares the hydrogen partial pressure on the measuring side with a known and fixed hydrogen partial pressure on the reference side. The most appropriate proton conducting solid electrolytes are perovskites, with doped strontium cerate ($SrCe_{0.95}Yb_{0.05}O_{3-d}$) and doped calcium zirconate ($CaZr_{0.9}In_{0.1}O_{3-d}$) being applied most frequently. Under the relevant experimental conditions, these materials exhibit predominant proton conductance. Electrodes are formed by covering the surface of the electrolyte with a catalytically active and electronically conducting material, for instance platinum. If two electrodes on different areas of the same electrolyte body are brought into contact with two media of different hydrogen contents, i.e., p'H2 and p"H2, a hydrogen concentration cell is formed:

p'H2|proton conducting solid electrolyte|p"H2

The potential difference generated may be described in terms of the well known Nernst equation, where U is the electromotive force (emf), R is the universal gas constant, T is the absolute temperature, F is Faraday's constant, and p"H2 and p'H2 are the hydrogen partial pressures at the measuring electrode and the reference electrode, respectively:

$$U = -\frac{RT}{2F} \ln \frac{p''_{H2}}{p'_{H2}}$$

Measuring the potential difference between the two electrodes and knowing the hydrogen partial pressure on the reference side, yields the unknown hydrogen partial pressure on the measuring side.

The incorporation of a hydrogen reference standard into the sensor unit constitutes a scientific and technological problem. Two different types of hydrogen sensors employing a solid electrolyte in conjunction with a hydrogen reference have thus far been reported.

The most straightforward approach consists in the utilisation of a gaseous hydrogen standard [T. Yajima, K. Koide, N. Fukatsu, T. Ohashi and H. Iwahara, Sensors and Actuators B 13-14, 697 (1993); T. Yajima, K. Koide, H. Takai, N. Fukatsu and H. Iwahara, Solid State Ionics 79, 333 (1995)]. This requires a cell design in which one side of the solid electrolyte is in contact with the medium to be analysed while the other side is continuously supplied with a reference gas mixture of known hydrogen partial pressure. A hydrogen analyser for use in molten aluminium, based on this principle and using $CaZr_{0.9}In_{0.1}O_{3-d}$ as the solid electrolyte, has been developed and commercialised. However, the use of a reference gas has been found awkward, and no breakthrough with this technology has been achieved.

In alternative approaches attempts have been made to fix the hydrogen partial pressure on the reference side by means of solid compounds or mixtures of solid compounds. The utilisation of hydrates like $Ce_2(SO_4)_3 \cdot 8H_2O$ and $AlPO_4 \cdot 0.34H_2O$ as the reference in conjunction with $SrCe_{0.95}Yb_{0.05}O_{3-d}$ and $CaZr_{0.9}In_{0.1}O_{3-d}$ as the solid electrolyte has been reported [H. Iwahara, H. Uchida, T. Nagano and K. Koide, Denki Kagaku 57, 992 (1989); T. Yajima, K. Koide, K. Yamamoto and H. Iwahara, Denki Kagaku 58, 547 (1990); T. Yajima, H. Iwahara, K. Koide and K. Yamamoto, Sensors and Actuators B 5, 145 (1991)]. However, incorporation of hydrates fixes the water rather than the hydrogen partial pressure and, even though some response behaviour to hydrogen has been observed in a few cases, these sensors require calibration and their signal stability is insufficient for practical applications. The utilisation of a calcium/calcium hydride (Ca/CaH2) mixture as the reference in contact with $SrCe_{0.95}Yb_{0.05}O_{3-\delta}$ as the solid electrolyte has been reported [M. Zheng and X. Zhen, Solid State Ionics 59, 167 (1993); M. Zheng and X. Zhen, Met. Trans. B 24, 789 (1993); M. Zheng and X. Chen, Solid State Ionics 70/71, 595 (1994)]. However, this combination was only found to work at comparatively low temperatures, i.e., below 600° C., and for relatively short times, i.e., a few hours, otherwise a continuous drift of the sensor signal towards zero was observed. The reason for the failure was identified to be the chemical instability of the electrolyte/reference interface. This causes a chemical reaction between the highly reducing reference material and the oxide-based solid electrolyte, which gradually converts the ion (proton) conductor into a mixed conductor and renders sensor readings impossible to interpret. Overall, no hydrogen sensor relying on a solid reference material has as yet proven to be viable in any practical application.

SUMMARY OF INVENTION

The invention provides apparatus and methods for sensing hydrogen concentration as defined in the appended independent claims. Preferred or advantageous features of the invention are set out in dependent subclaims.

The present invention may thus provide an apparatus for measuring hydrogen concentration, comprising a proton-conducting solid electrolyte in conjunction with a self-contained and hermetically sealed metal/hydrogen reference standard, of which the content and/or the spatial distribution of oxygen is appropriate substantially to prevent chemical reaction between the solid electrolyte and the reference material, particularly at the interface there between.

The present invention may thus advantageously provide a sensor with a novel hydrogen standard that establishes a defined and reproducible reference hydrogen partial pressure and ensures chemical stability of the electrolyte/reference interface.

The present invention is based on the realisation that, first, a metal/hydrogen two-phase/two-component mixture (being a solution of hydrogen in the metal such that, under the conditions of use of the apparatus, the solution lies within a two-phase field of the metal-hydrogen phase diagram) may be used as an internal hydrogen standard in sensors employing an oxide-based proton-conducting solid electrolyte, because this type of mixture is able to fix the hydrogen partial pressure inside an encapsulated volume adjacent to the electrolyte and, second, may advantageously enable the interface between the electrolyte and the reference to be chemically stable. It is further realised that, in a preferred embodiment, the second issue may be fulfilled by maintaining a suitable oxygen activity in the reference material, which is both sufficiently high in order to guarantee chemical stability in contact with the oxide-based electrolyte, so the proton conducting properties of the latter are not affected, and sufficiently low in order not to invalidate the two-phase/two-component approach. It should be noted that the appropriate oxygen concentration, or range of oxygen concentration, required to achieve this in any particular case may depend not only on the oxygen activity required for proper operation of the reference standard but also on the chemical stability of the electrolyte material.

According to one embodiment of the invention, the proton conducting solid electrolyte is a perovskite, preferably $SrCe_{0.95}Yb_{0.05}O_{3-\delta}$ or $CaZr_{0.9}In_{0.1}O_{3-\delta}$, and the metal component of the metal/hydrogen reference system is titanium, zirconium or hafnium. For these materials the above requirements may readily be met, as will be pointed out in the following.

The metal in the reference standard may be an alloy and the reference standard may contain other elements which affect its phase diagram. Nevertheless, the quantitative predominance of the respective metal and hydrogen in the two-phase mixture guarantee that the chemical potential and the activity of the two components, i.e., the respective metal and hydrogen, are thermodynamically fixed in terms of Gibbs' phase rule. This means that, within the range of the two-phase area (within which the two phases of the metal can coexist), the hydrogen activity is independent of the composition of the reference system and also does not change when the composition undergoes small variations during sensor operation. The hydrogen activity of the reference system may be determined from literature data and is only a function of temperature. Knowledge of the reference hydrogen partial pressure for the given temperature permits direct determination of the hydrogen partial pressure on the measuring side. In case of titanium, the $\alpha$-titanium/$\beta$-titanium two-phase region is preferred whilst the $\beta$-titanium/$\delta$-titanium two-phase region is less suitable because the corresponding hydrogen partial pressures are beyond atmospheric pressure. Regarding zirconium, both the $\alpha$-zirconium/$\beta$-zirconium and the $\beta$-zirconium/$\delta$-zirconium two-phase areas may be used, but the latter is preferred because of its extended composition range at elevated temperatures. Concerning hafnium, only the $\alpha$-hafnium/$\delta$-hafnium two-phase region is appropriate.

Secondly, a chemically stable interface between the solid electrolyte and the reference material may advantageously be ensured. It is important to note that even minute changes in the oxygen concentration may have a dramatic impact on the electrochemical properties of oxide-based proton conducting solid electrolytes. In fact, the release of small amounts of oxygen has been shown to convert these materials from pure proton conductors into mixed conductors, oxygen ion conductors or semiconductors, which makes them inappropriate for the application envisaged. Accordingly, very reactive metals like alkali metals, alkaline earth metals and rare earth metals, which also form two-phase areas with hydrogen, are not preferred for use as the reference material, since they reduce the oxide-based solid electrolyte at elevated temperatures. Even less reactive metals like titanium, zirconium and hafnium may, in their pure state, be sufficiently reducing to affect the performance of the solid electrolyte. However, and in contrast to the previously mentioned metals, the reactivity of titanium, zirconium and hafnium may be lowered considerably through the presence of only small amounts of oxygen. In this way, the electrolyte/reference interface may be rendered chemically stable, whilst the two-component/two-phase approach is not compromised.

The signal of a sensor, which is constructed in accordance with the above requirements, may advantageously be used to determine directly the hydrogen content in a fluid medium. If the composition of the medium needs to be controlled, the composition may then be varied until the required signal is recorded.

DESCRIPTION OF THE INVENTION

Figure 1:
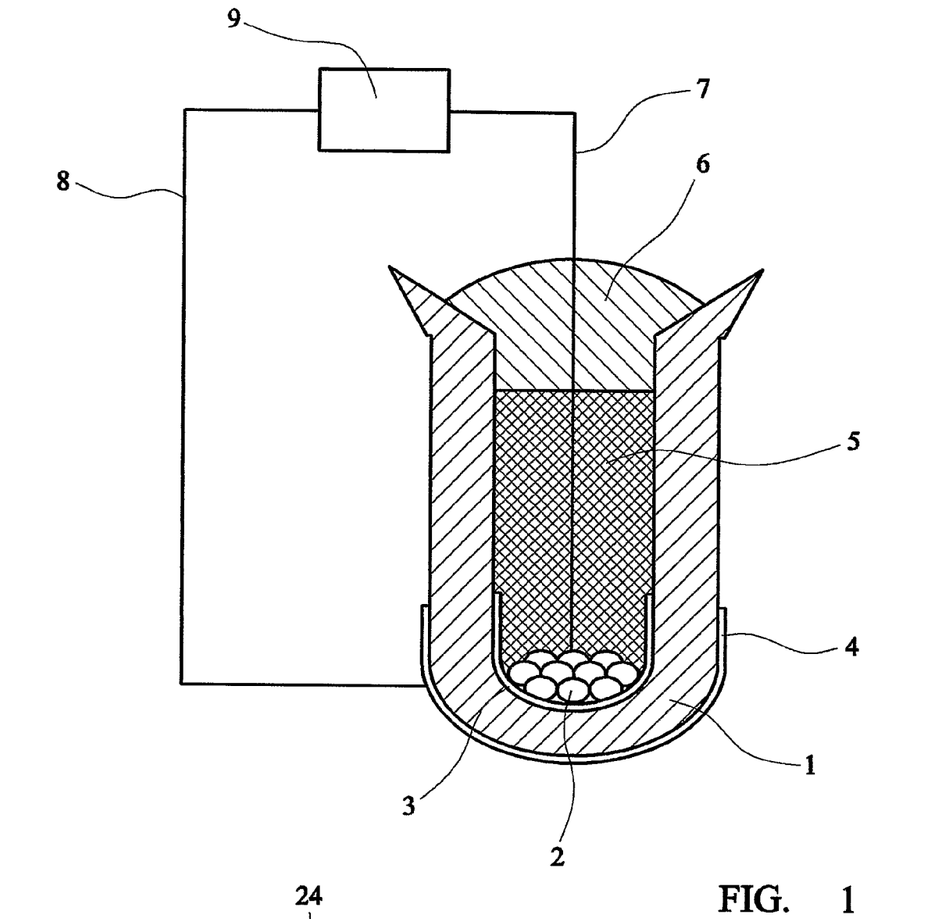
FIG. 1 is a schematic illustration of an apparatus according to an embodiment of the invention.

FIG. 1 shows a schematic illustration of a preferred embodiment of the invention, comprising a solid electrolyte body 1, a reference material 2, an inert packing material 5, a glass seal 6, a catalytic coating at a reference electrode 3, a catalytic coating at a measuring electrode 4, a lead to the reference electrode 7, a lead to the measuring electrode 8, and an electronic measuring unit 9.

The solid electrolyte is shaped as a tube, closed at one end, with a length of about 20 mm and a diameter of about 5 mm, but it may be appreciated that the precise dimensions are not critical. This solid electrolyte shape may be described as a thimble. In the preferred embodiment, the electrolyte material is a perovskite. A catalytic coating may be applied to the interior and the exterior surfaces of the electrolyte tube. Electrical leads may be placed on both surfaces. In the preferred embodiment, the catalytic coatings and the electrical leads are made from platinum.

Typically, about 50 to 200 mg of the reference material may be used, but it may be appreciated that the exact quantity is not critical. Lower amounts as small as 10 mg or 15 mg may also be used, but 70 mg to 90 mg or about 80 mg has been found to be most effective. In the preferred embodiment, the reference material is titanium/hydrogen, zirconium/hydrogen or hafnium/hydrogen and is placed inside the electrolyte tube.

The reference material is encapsulated by means of a suitable sealing material. When applying an oxide-based sealing glass, the silicon content must be low in order to prevent detrimental reactions between the hydrogen in the reference compartment and the silicon in the glass, which would result in decomposition of the reference material. In the preferred embodiment, a silicon-free glass based on the oxides of aluminium, barium, boron, calcium and magnesium is used. The direct contact of the reference material and the sealing material may be detrimental. In the preferred embodiment, an inert packing material like pure calcium zirconate or yttrium oxide serves as a separator between both these components.

It may be appreciated that other designs of the invention may likewise be employed. These may include layered designs, in which use is made of pellets or films, which may be printed. In these, the solid electrolyte body, the reference material and the inert packing material (if required) are used in a parallel arrangement, such as in a stack of layers. This arrangement or stack is sealed, such that only the measuring electrode on the electrolyte body is exposed to the ambient medium.

Figure 5:
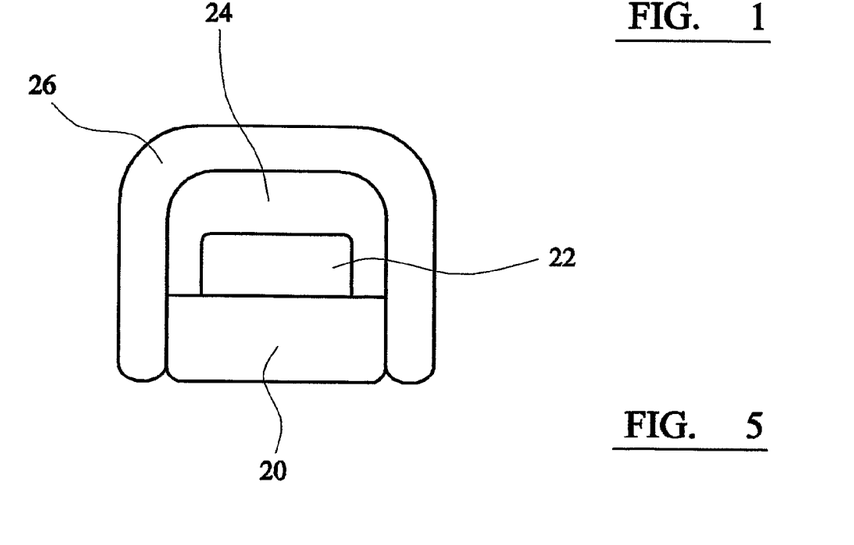
FIG. 5 is a schematic illustration of an apparatus according to a second embodiment of the invention.

An example is shown in FIG. 5, in which an electrolyte layer 20 is placed beneath a reference standard layer 22, both formed as disc-shaped pellets. A packing material 24 covers the upper and side surfaces of the reference standard layer and the stack thus formed is sealed in a glass casing 26, leaving only one face of the electrolyte exposed for access to media in which hydrogen concentration is to be measured. The packing material separates the reference standard layer from the sealing glass to prevent chemical degradation. Electrical connections to the probe are formed by layers applied to the upper and lower electrolyte surfaces, in the same way as described in other embodiments.

Preparation of the apparatus is straightforward and can be performed in two ways. The first procedure consists of two steps. In the first step, a quantity of titanium, zirconium or hafnium metal is inserted into the open end of the solid electrolyte tube, or thimble, and a seal across the open end of the tube is created by melting and then solidifying a solder glass under an atmosphere of an inert gas or hydrogen gas or a mixture thereof. The residual oxygen content should be low in order to avoid oxidation of the metal. The seal ensures that the metal is in contact with the electrolyte but hermetically sealed from the environment. In the second step, and depending on the amount of hydrogen present in the reference compartment after sealing, an electric current is applied such that hydrogen is electrochemically transported into or out of the reference compartment until the metal to hydrogen atomic ratio is suitable for the metal/hydrogen mixture to function as a reference standard for hydrogen. This method of preparation is preferred for the use of titanium/hydrogen as the reference system.

The second procedure consists of only one step. In this, a quantity of titanium, zirconium or hafnium metal is inserted into the open end of the solid electrolyte tube, or thimble, and a seal is created by melting and solidifying a solder glass under a hydrogen-containing atmosphere while, simultaneously, the reference is being formed through hydrogen uptake by the metal from the gas. In order for the metal/hydrogen mixture to function as a standard for hydrogen, it is important to match the melting temperature of the glass and the hydrogen content of the gas atmosphere such that, after formation of the seal, the metal to hydrogen atomic ratio in the metal/hydrogen reference is inside the desired two-phase area. This method of preparation is preferred for the use of zirconium/hydrogen or hafnium/hydrogen as the reference system.

After preparation of the apparatus according to one of the above procedures and prior to use, preconditioning is carried out at elevated temperature, preferentially beyond 700° C., in a humidified gas atmosphere of low hydrogen partial pressure, preferentially below 1% by volume.

The apparatus may be placed directly into the medium to be analysed, which may be stagnant or flowing, at a temperature sufficient for the solid electrolyte to conduct ionically. Preferably the temperature is in the range of 500° C. to 900° C. The sensors were found to detect hydrogen contents from at least 100 ppm to 100% by volume.

EXAMPLES

High density ceramic thimbles of indium oxide doped calcium zirconate ($CaZr_{0.9}In_{0.1}O_{3-d}$) were obtained through isostatic pressing of a suitable powder and sintering at 1600° C. in air for 8 h. Porous platinum electrodes were generated by firing a platinum-containing ink at 1000° C. in air for 1 h. Platinum lead wires were attached to both platinum coatings.

Example 1

Figure 2:
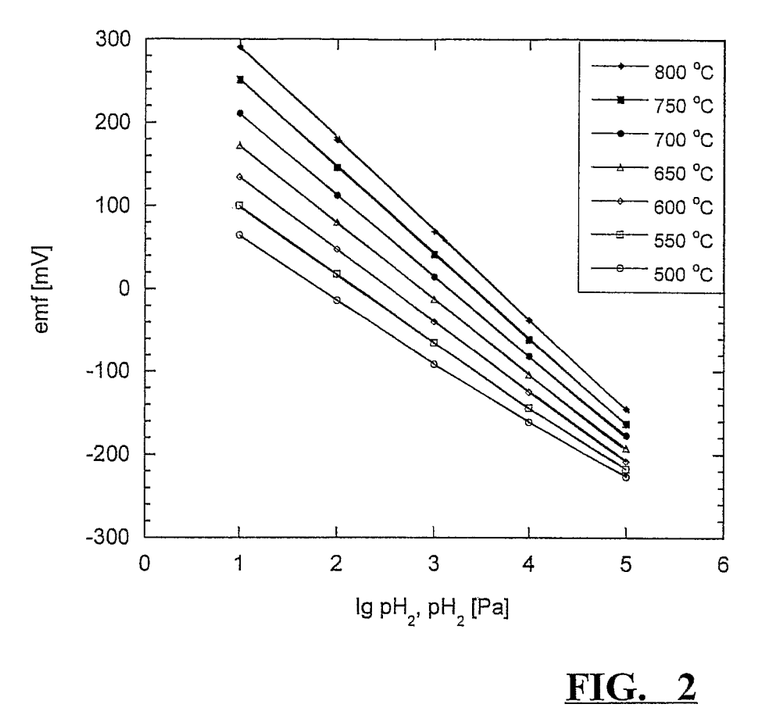
FIG. 2 is a plot of the measured cell potential when using sensors with the $\alpha$-titanium/$\beta$-titanium+hydrogen (+oxygen) reference system to measure hydrogen concentration in hydrogen/argon gas mixtures of known hydrogen concentration at different temperatures.

40 mg of titanium metal pieces, cut from a grit-blasted sheet of commercial grade 4 titanium metal with a known bulk oxygen content of 3600 ppm by mass, were placed inside a ceramic calcium zirconate thimble. (Grit-blasting was carried out to clean the surfaces of the as-received titanium metal specimen.) The interior of the thimble was then filled with undoped calcium zirconate powder which is inert and acts as a packing material. This was covered with a layer of a laboratory-made, silicon-free, sealing glass powder, which has a melting point of approximately 930° C. To melt the glass and form the seal, the arrangement was heated to around 940° C. in an alumina tube under pure hydrogen. Prior to application, the hydrogen was passed through calcium sulphate to remove traces of moisture and through a suitable metal scrubber to ensure low residual oxygen content. The unit was then exposed to a 1% by volume hydrogen in argon gas mixture at 700° C. and coulometric titration was performed. To that end, a direct current of around 60 mA, this typically corresponding to voltages in the range of a few hundred millivolts, was applied for about 200 h, with the inner electrode connected to the positive terminal and the outer electrode connected to the negative terminal. By way of this procedure, a quantity of hydrogen was removed from the reference compartment, such that the titanium to hydrogen ratio established in the reference system was inside the α-titanium/β-titanium two-phase area. After preparation, the sensor was preconditioned at 800° C. in argon, which had been humidified by passing through a water bubbler at room temperature, for at least 1 h. Sensor measurements were performed between 500 and 800° C. in hydrogen/argon mixtures with hydrogen contents of 10 ppm, 100 ppm, 1%, 10% and 100% by volume. Measured emfs are shown in FIG. 2. The data are in good agreement with thermodynamically expected values. Sensor signals were stable, with a drift of typically less than 1 mV/d, and the response time to changes in temperature and hydrogen partial pressure was in the order of minutes. Variations in the results for different sensors were found to be less than 5%.

Notably, although this good performance was obtained with grade 4 titanium, no stable sensor readings were obtained when pieces of grit-blasted grade 1 or grade 2 titanium metal sheets with bulk oxygen contents of 1450 and 1780 ppm by mass, respectively, were applied as the metal component in the reference system. This suggests the importance of the oxygen content in the reference system for proper sensor performance.

This observation that the indium oxide doped calcium zirconate electrolyte was reduced by grade 1 or grade 2 titanium but not by grade 4 titanium suggests an acceptable range of oxygen concentration for this combination of materials. However, different electrolyte materials used with titanium-based reference standards may require different oxygen concentrations in the titanium. For example, a more stable electrolyte may tolerate lower oxygen concentrations in the titanium.

Example 2

Figure 3:
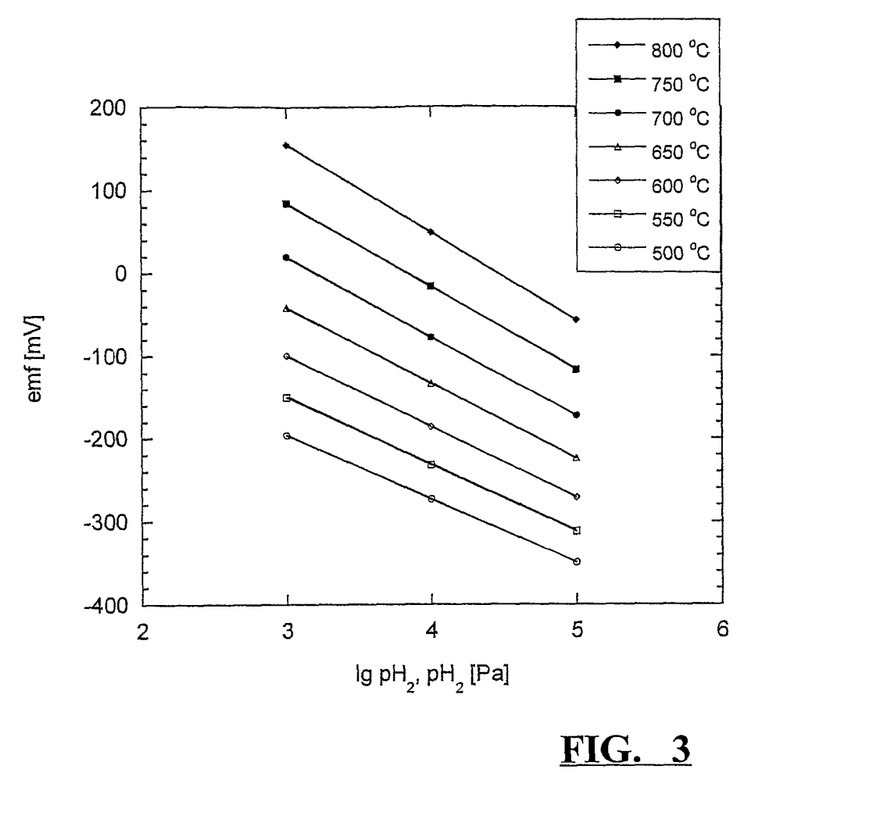
FIG. 3 is a plot of the measured cell potential when using sensors with the $\beta$-zirconium/$\delta$-zirconium+hydrogen (+oxygen) reference system to measure hydrogen concentration in hydrogen/argon gas mixtures of known hydrogen concentration at different temperatures.

About 100 mg of zirconium metal were cut from a commercial zirconium wire with a known bulk oxygen content of 1500 ppm by mass and placed inside a ceramic calcium zirconate thimble. The interior of the thimble was filled with yttrium oxide powder, which acts as an inert packing material, and this was covered with a layer of silicon-free sealing glass powder as described in example 1. To melt the glass and form the seal, the arrangement was heated to around 940° C. in an alumina tube under pure hydrogen. By way of this procedure, a zirconium to hydrogen ratio inside the β-zirconium/δ-zirconium two-phase area was established directly. Preconditioning of the sensor was carried out as described in example 1. Sensor measurements were performed between 500° C. and 800° C. in hydrogen/argon mixtures with hydrogen contents of 1, 10 and 100% by volume. Measured emfs are shown in FIG. 3. Agreement with thermodynamic expectations, signal stability and comparability between individual sensors were even better than what was found, and reported in example 1, for sensors relying on the titanium/hydrogen reference system.

Notably, the above zirconium material could be employed successfully both in the as-received and in the grit-blasted state. In contrast, a different zirconium wire, with a bulk oxygen content of 1010 ppm by mass, was found to work successfully only in the as-received state, then providing similar results to the ones shown in FIG. 3. When applying the same zirconium material after grit-blasting, no stable signals were achieved. This suggests that the particular material possesses an oxygen-rich surface layer which renders the electrolyte/reference interface stable if used in the as-received state, but that the bulk oxygen content is too low to allow for a stable interface once the outer layer is removed.

Example 3

Figure 4:
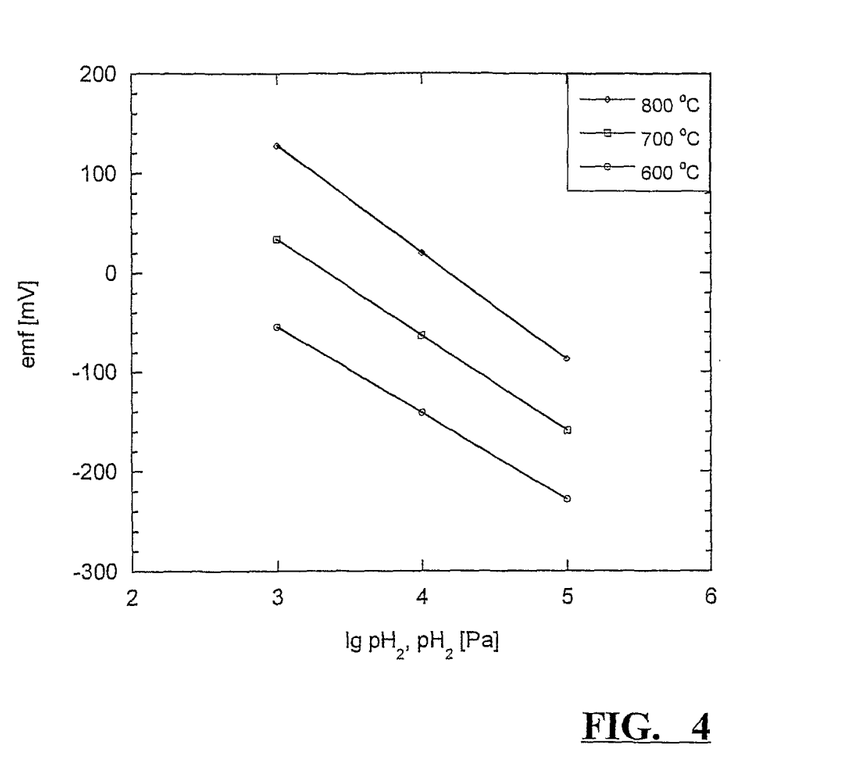
FIG. 4 is a plot of the measured cell potential when using sensors with the $\alpha$-hafnium/$\delta$-hafnium+hydrogen (+oxygen) reference system to measure hydrogen concentration in hydrogen/argon gas mixtures of known hydrogen concentration at different temperatures.

About 200 mg of hafnium metal were cut from a commercial hafnium wire with a known oxygen content of 230 ppm by mass and placed inside a ceramic calcium zirconate thimble. 1.0 mg of titanium dioxide was added. The interior of the thimble was filled with yttrium oxide powder, which acts as an inert packing material, and this was covered with a layer of a laboratory-made silicon-free sealing glass powder, which has a melting point of approximately 970° C. To melt the glass and form the seal, the arrangement was heated to around 980° C. in an alumina tube under pure hydrogen. By way of this procedure, a hafnium to hydrogen ratio inside the α-hafnium/δ-hafnium two-phase area was established directly. Preconditioning of the sensor was carried out as described in example 1. Sensor measurements were performed between 600 and 800° C. in hydrogen/argon mixtures with hydrogen contents of 1, 10 and 100% by volume. Measured emfs are shown in FIG. 4. Sensor performance was again found to be good.

Notably, the above hafnium wire could be used neither in the as-received nor in the grit-blasted state. This suggests that, firstly, the bulk oxygen content is too low to allow for a stable electrolyte/reference interface and, secondly, that the oxygen-rich surface layer, if any, is too thin to prevent oxygen uptake of the reference material from the electrolyte. So, it is only through the formation of a passivating surface layer, brought about by the decomposition of titanium dioxide in the presence of hydrogen gas and subsequent precipitation of oxygen-containing species on the hafnium wire, that stability of the electrolyte/reference interface is provided.

We claim:

1. An apparatus for measuring hydrogen concentration at a temperature above 500° C., comprising an oxide-based proton-conducting solid electrolyte in conjunction with, or in contact with, a self-contained, sealed, metal/hydrogen reference standard comprising a reference material, which is zirconium or an alloy of zirconium, wherein the zirconium or zirconium alloy contains at least 1010 ppm of oxygen, with a metal to hydrogen atomic ratio such that two phases of the metal/hydrogen solution are present, contained and hermetically sealed within a reference compartment, wherein the reference material is solid and is surrounded by an oxygen-rich layer or comprises an oxygen-rich layer at its surface that prevents reaction between the solid electrolyte and the reference material, wherein the oxygen activity in the reference material is sufficiently low that the two phases of the metal/hydrogen solution are retained during use of the apparatus to measure hydrogen concentration, and wherein the reference standard is sealed with a sealing material that is chemically stable in a hydrogen containing gas at elevated temperatures above 500° C. and provides a seal above 500° C., wherein said sealing material is a silicon-free oxide glass that comprises one or more of the oxides of aluminum, barium, boron, calcium and/or magnesium.

2. The apparatus according to claim 1, wherein the proton conductor is a perovskite.

3. The apparatus according to claim 2, wherein the proton conductor is doped calcium zirconate or doped strontium cerate.

4. The apparatus according to claim 1, wherein the two-phase area is that of α-zirconium/β-zirconium or β-zirconium/δ-zirconium.

5. The apparatus according to claim 1, wherein the oxygen-rich layer on the solid reference material either originates from the production process of the metal or is generated subsequently by means of a chemical reaction.

6. The apparatus according to claim 5, wherein the chemical reaction to generate an oxygen rich layer on the particles of a solid reference material comprises heating the metal of the reference system or the metal/hydrogen reference mixture in the presence of a metal oxide.

7. The apparatus according to claim 1, wherein the solid electrolyte is coated with a catalyst at the point of contact with the electrode.

8. The apparatus according to claim 7, wherein the catalytic coating is platinum.

9. The apparatus according to claim 1, wherein an inert packing material is used as a separator between the reference material and the sealing material.

10. The apparatus according to claim 9, wherein the inert packing material is calcium zirconate or yttrium oxide.

11. The apparatus according to claim 1, wherein the reference standard is created in two steps by, firstly, hermetically sealing the metal into the reference compartment and, secondly, passing hydrogen electrochemically through the solid electrolyte to form the metal/hydrogen reference material.

12. The apparatus according to claim 1, wherein the metal/hydrogen reference standard is generated in one step, by heating the metal in the presence of a hydrogen containing gas while simultaneously forming a seal to close the reference compartment.

13. The apparatus according to claim 1, wherein the sensor, after preparation and prior to use, is preconditioned with a humidified gas of low hydrogen content at elevated temperatures.

14. The apparatus according to claim 13, wherein the preconditioning is performed in a humidified mixture of 1% hydrogen or less in argon at 700° C. or more for 15 min or more.

15. The apparatus according to claim 1, wherein the sealing material has a melting temperature below 1200° C.

16. A method for measuring hydrogen concentration comprising the steps of: providing a probe comprising an oxygen-based proton-conducting solid electrolyte in conjunction with, or in contact with, a sealed, or self-contained, metal/hydrogen reference standard comprising a reference material, which is zirconium or an alloy of zirconium, wherein the zirconium or zirconium alloy contains at least 1010 ppm of oxygen, with a metal to hydrogen atomic ratio such that two phases of the metal/hydrogen solution are present, contained and hermetically sealed within a reference compartment, wherein the metal/hydrogen mixture is solid and is surrounded by an oxygen-rich layer or comprises an oxygen-rich layer at its surface that prevents reaction between the solid electrolyte and the reference material, wherein the oxygen activity in the reference material is sufficiently low that the two phases of the metal/hydrogen solution are retained during use of the apparatus to measure hydrogen concentration and wherein the reference standard is sealed with a sealing material that is chemically stable in a hydrogen containing gas at elevated temperatures above 500° C. and provides a seal above 500° C., wherein said sealing material is a silicon-free oxide glass that comprises one or more of the oxides of aluminum, barium, boron, calcium and/or magnesium;
  bringing the electrolyte into contact with a hydrogen concentration to be measured, at a temperature above 500° C.; and measuring a voltage generated across the electrolyte between the hydrogen concentration and the reference standard; or
  comprising the steps of: providing a probe comprising an oxygen-based proton-conducting solid electrolyte in conjunction with, or in contact with, a sealed, or self-contained, metal/hydrogen reference standard comprising a reference material, which is titanium or hafnium, or an alloy of titanium or hafnium, with a metal to hydrogen atomic ratio such that two phases of the metal/hydrogen solution are present, contained and hermetically sealed within a reference compartment, wherein the metal/hydrogen mixture is solid and is surrounded by an oxygen-rich layer or comprises an oxygen-rich layer at its surface that prevents reaction between the solid electrolyte and the reference material, wherein the oxygen activity in the reference material is sufficiently low that the two phases of the metal/hydrogen solution are retained during use of the apparatus to measure hydrogen concentration and wherein the reference standard is sealed with a sealing material that is chemically stable in a hydrogen containing gas at elevated temperatures, wherein said sealing material is a silicon-free oxide glass that comprises one or more of the oxides of aluminum, barium, boron, calcium and/or magnesium; bringing the electrolyte into contact with a hydrogen concentration to be measured, at a temperature above 500° C.; and measuring a voltage generated across the electrolyte between the hydrogen concentration and the reference standard.

17. An apparatus for measuring hydrogen concentration at a temperature above 500° C., comprising an oxide-based proton-conducting solid electrolyte in conjunction with, or in contact with, a self-contained, sealed, metal/hydrogen reference standard comprising a reference material, which is titanium or hafnium, or an alloy of titanium or hafnium, with a metal to hydrogen atomic ratio such that two phases of the metal/hydrogen solution are present, contained and hermetically sealed within a reference compartment, wherein the reference material is solid and is surrounded by an oxygen-rich layer or comprises an oxygen-rich layer at its surface that prevents reaction between the solid electrolyte and the reference material, wherein the oxygen activity in the reference material is sufficiently low that the two phases of the metal/hydrogen solution are retained during use of the apparatus to measure hydrogen concentration, and wherein the reference standard is sealed with a sealing material that is chemically stable in a hydrogen containing gas at elevated temperatures above 500° C. and provides a seal above 500° C., wherein said sealing material is a silicon-free oxide glass that comprises one or more of the oxides of aluminum, barium, boron, calcium and/or magnesium.

18. The apparatus according to claim 17, wherein the titanium or titanium alloy contains more than 1780 ppm of oxygen.

19. The apparatus according to claim 17, wherein the proton conductor is a perovskite.

20. The apparatus according to claim 19, wherein the proton conductor is doped calcium zirconate or doped strontium cerate.

21. The apparatus according to claim 17, wherein the two-phase area is that of $\alpha$-titanium/$\beta$-titanium or $\alpha$-hafnium/$\delta$-hafnium.

* * * * *